US006487817B2

(12) United States Patent
Airaudi (10) Patent No.: US 6,487,817 B2
(45) Date of Patent: Dec. 3, 2002

(54) ELECTRONIC DEVICE TO DETECT AND DIRECT BIOLOGICAL MICROVARIATIONS IN A LIVING ORGANISM

(75) Inventor: Oberto Airaudi, Cuceglio (IT)

(73) Assignee: Music of the Plants, LLP, Hallandale, FL (US)

(*) Notice: Subject to any disclaimer, the term of this patent is extended or adjusted under 35 U.S.C. 154(b) by 11 days.

(21) Appl. No.: 09/849,756

(22) Filed: May 4, 2001

(65) Prior Publication Data

US 2002/0026746 A1 Mar. 7, 2002

Related U.S. Application Data

(63) Continuation-in-part of application No. 09/324,402, filed on Jun. 2, 1999, now abandoned.
(51) Int. Cl.[7] .............................. A01G 7/04; G10H 5/00
(52) U.S. Cl. ......................... 47/58.1 R; 47/1.3; 84/600
(58) Field of Search ............................... 47/58.1 R, 1.3; 84/600

(56) References Cited

U.S. PATENT DOCUMENTS 3,852,914 A * 12/1974 Levengood ................. 324/71.1
4,883,067 A * 11/1989 Knispel et al. ............... 600/28
4,919,143 A * 4/1990 Ayers .......................... 128/905
5,253,168 A * 10/1993 Berg ........................... 128/905
5,343,871 A * 9/1994 Bittman et al. ............. 128/905
6,144,954 A * 11/2000 Li ................................ 706/46

FOREIGN PATENT DOCUMENTS

EP          477781 A1 *  1/1992  ............ A01G/7/04
GB         2210765 A  *  6/1989  ............ A01G/7/04

* cited by examiner

*Primary Examiner*—Peter M. Poon
*Assistant Examiner*—Son T. Nguyen
(74) *Attorney, Agent, or Firm*—Welsh & Katz, Ltd.

(57) ABSTRACT

A method and apparatus are provided for using microvariations of a biological living plant organism to generate music. The method includes the steps of detecting a plant microvoltage across a varying resistance of the biological living plant organism within a Wheatstone bridge, generating a feedback signal from an output of an external MIDI sound generator, subtracting the feedback signal from the plant microvoltage to provide a difference signal and providing the difference signal as a drive signal to the MIDI sound generator to generate music.

21 Claims, 10 Drawing Sheets

INPUT AMPLIFIER

RES: 1/4X 1%
COND: MKT

| FIG. 7a | FIG. 7b | FIG. 7c |

BLOCK DIAGRAM

ELECTRONIC DEVICE TO DETECT AND DIRECT BIOLOGICAL MICROVARIATIONS IN A LIVING ORGANISM

This application is a continuation-in-part of U.S. patent application Ser. No. 09/324,402, filed on Jun. 2, 1999 now abandoned.

FIELD OF THE INVENTION

The field of the invention relates to living organisms and more particularly to the detection in microvariation produced by the living organisms.

BACKGROUND OF THE INVENTION

In the medical arts there are systems for detection of biologic and bioclimatic variations, such as electrocardiographs, electroencephalographs, etc. There are also other systems to detect biological and bioclimatic variations used for the automatic control of greenhouses and servocontrols which, for that purpose, use sensors which assesses environmental conditions, such as the humidity of the environment or of the earth. This invention is different from all of the above because it uses the living organism itself as the signal source of the sensor and the user of the signal it produces.

SUMMARY

A method and apparatus are provided for using microvariations of a biological living plant organism to generate music. The method includes the steps of detecting a plant microvoltage across a varying resistance of the biological living plant organism within a Wheatstone bridge, generating a feedback signal from an output of an external MIDI sound generator, subtracting the feedback signal from the plant microvoltage to provide a difference signal and providing the difference signal as a drive signal to the external MIDI sound generator to generate musical tones via a synthesizer.

BRIEF DESCRIPTION OF THE DRAWINGS

APPENDIX I provides object code that may be used by the microcontroller of FIG. 3.

DETAILED DESCRIPTION OF A PREFERRED EMBODIMENT

Disclosed herein is apparatus that may be used to detect and translate into useable terms a micro variation detectable in any biologic living organism. Such variation can be in resistance, conductivity, tension, pressure, chromatic value, magnetism, etc.

The disclosed invention has been found effective in detecting and translating into useable terms microvariations detectable in any living organism. Living organisms, and more specifically plants, are believed capable of varying their internal bio-electric state as a consequence of external situations. Plants are, therefore, capable of some sort of rudimentary "feelings".

Figure 1:
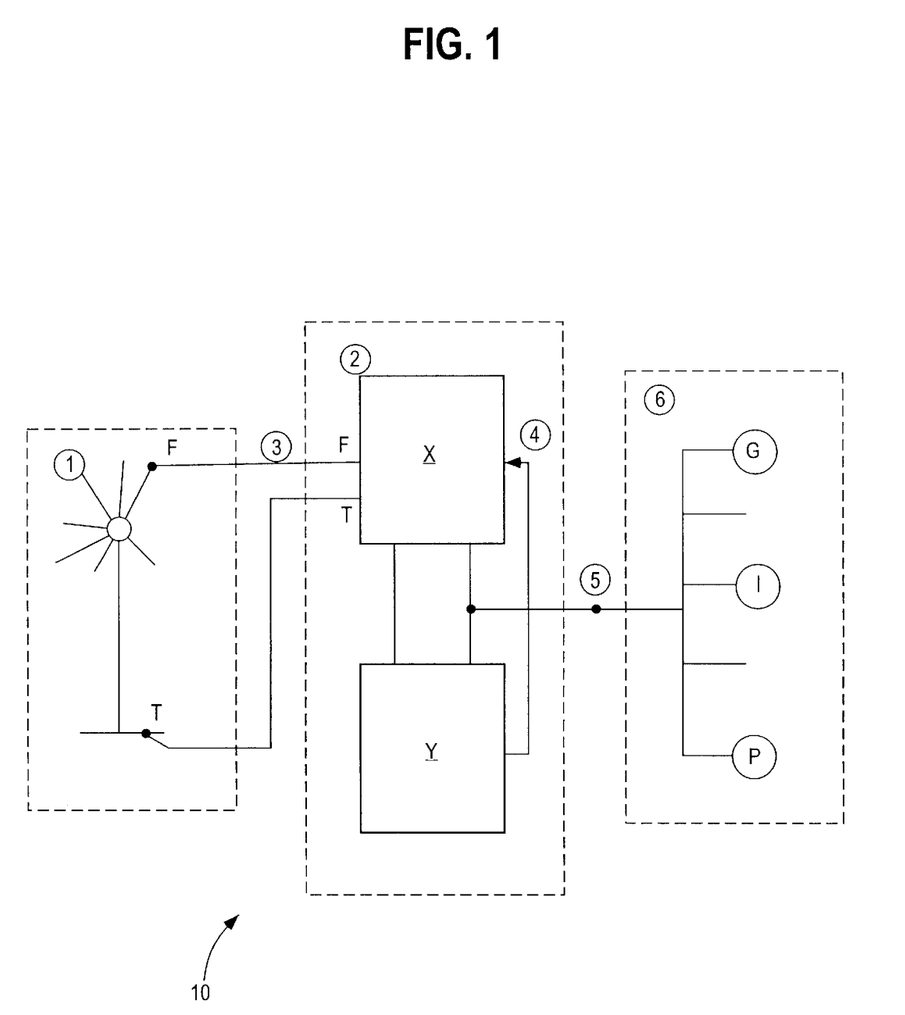
FIG. 1 depicts a block diagram of a system for controlling the environment of a living organism in accordance with an illustrated embodiment of the invention.

FIG. 1 shows a block diagram of the apparatus 10, generally used for detecting, and translating into useable terms, microvariations detectable in any living organism. FIG. 1 shows a living biologic organism 1, which in this case is represented by a plant . The electrodes "F" and "T" of block #1 have been applied to two parts of the plant, which are not touching each other. The electrodes F, T attached to the plant are made of conductive materials. The electrodes F, T form two poles which detect the variation in electrical resistivity of the subject 1. In block #2 a general (i.e., a non-specific) diagram of the control and management circuit of the signals detected by electrodes F, T, as they are received through the portal 3, is indicated. In more detail, by reference to "X" in block #2 we are indicating the circuits which detect the variations in resistivity, amplified as needed, and by reference to "Y" we indicate the circuit "Y" which maintains the outgoing level of electrical tension (voltage) within the confines of the predefined field of measurement, via a counter reaction indicated by #4 applied to circuit "X". By #5, we indicate the value or amounts of outgoing tension which is later sometimes indicated by the terminology in quotation marks, "via out", which follows the variation in resistivity of the subject 1 as detected by sensors F, T. #6 indicates the system of interfacing with the outside world created and realized with systems that are available on the market, such as for example, "G", tension (i.e., voltage) controlled audio frequency generator, or the letter "I" which represents a musical instrument digital interface (MIDI), or "P" which indicates traditional or computerized portals of interface or other.

If we analyze-in detail the block diagram in FIG. 1 and if we also take into consideration block #2, we can see that it contains an entrance represented by the portal (input) #3, and an exit (output) represented by #5. The input #3 contains two terminals: one called "F", which through the electrode made of a conductive material of the right proportion is applied on the leaves; and another, represented by the letter "T"; which through a similar electrode is applied to the roots via insertion into the soil, where the subject 1 finds root. Whatever the situation, the contact is always created in two distinct points, (that are not connected directly one to another) of the living organism 1 which is under analysis. Another example of this may be two fingers of a human hand.

Figure 2:
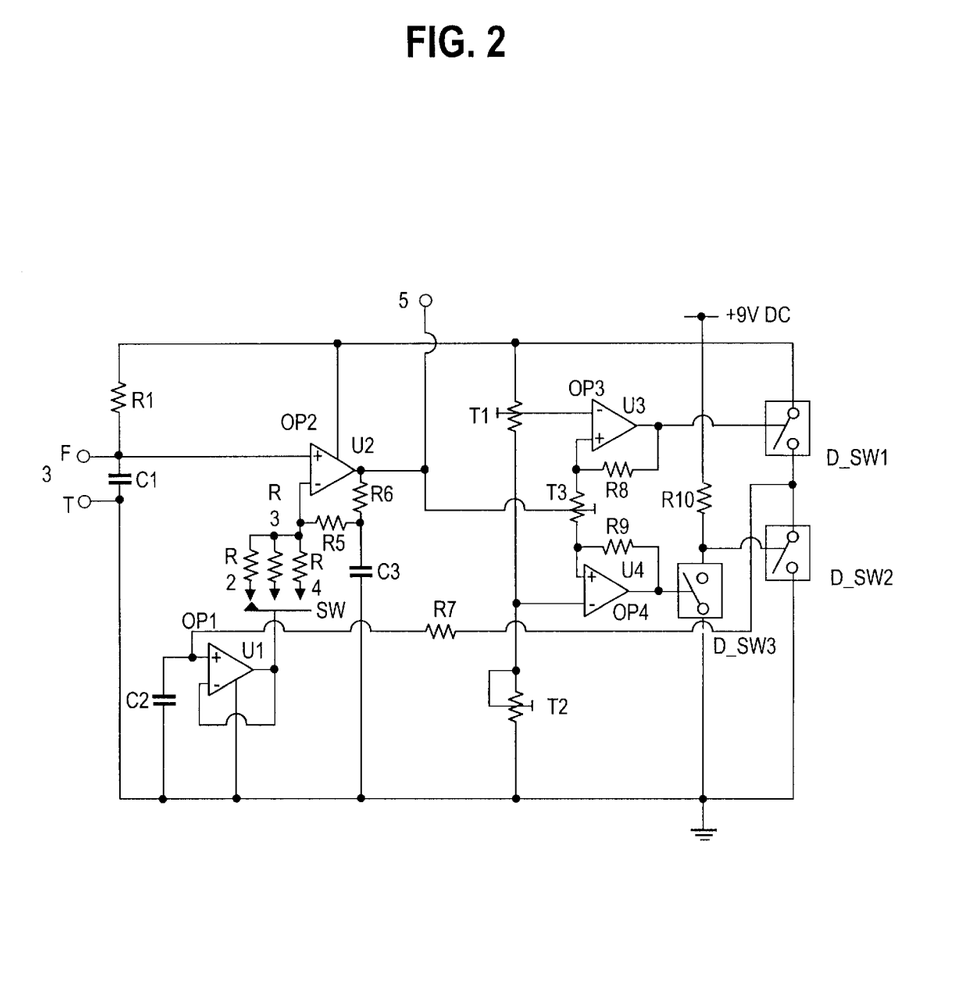
FIG. 2 depicts a schematic of a circuit that may be used by the system of FIG. 1.

Let us now analyze the circuit represented by FIG. 2, which describes, in one of the many possible configurations, block #2 of FIG. 1. We can see that the circuit is powered by a battery whose power can range from 3 to 12 volts. The electrical power which flows through and feeds the circuit of block #2 also brings a very weak current through resistor R1 to the tips of electrodes "F" and "T" that are linked (coupled)

to the plant. C1 is a condenser which works as a filter for any possible electrical disturbance present in the environment. The 9 volts of tension which reach the subject, through electrodes "F" and "T" are influenced by the actual condition of the plant itself.

To continue: the condition as referred to in the previous sentence could be of many kinds. For example, the condition referred to would be electrical, conductive, resistive, biochemical, biological, or anything else that may influence the value previously mentioned.

The variation in tension at the tips of the electrodes "F" and "T" are applied to the non-inverting entrance of the operational unit (amplifier) designated by "OP2", which is used as an amplifier of these same tension variations. As the relationship of amplification is defined by the partition of the resistors R5 and R6 together with the resistors R2, R3 and R4, the value of the amplification is determined manually by the operator with a three-position switch called "SW". It is therefore possible to use a minimum, average, or a maximum amplification, based upon switch position.

The couple formed by the resistor R6 together with the condenser C3 constitutes a second filter, or filtering cell, for any possible electrical disturbance. The operational unit "OP1" is connected to amplification #1 (i.e., provide unity gain) because its exit is linked to its inverting entrance. Therefore, such exit will have the same tension value present in its non-inverting entrance (i.e., the tension present at the tip (upper connection) of condenser C2).

The connection configuration of condenser C2 and of operation unit "OP1" allows the correction and the balancing in an automatic manner of the tension value present in terminal "V1", of the operational unit "OP1", whenever the variation in tension detected by electrodes "F" and "T" amplified by operational unit OP2 brings the exit of such operational unit OP2 to a state of positive saturation entitled "$V_{max}$", (i.e., equal to a tension of the electrical power supply) or negative "$V_{min}$" (i.e., equal to a tension of the mass (ground)). In this way, the circuit is brought back into a correct manner of functioning. Because of this kind of configuration, the level of tension, of V1, present at the exit of such amplification, operational unit OP1 is equal to the level of tension present at the tips of the condenser C2. Such tension V1 is applied through the three position switch SW to the inverting entrance of the operational unit OP2, thus producing a specific, negative reaction that is able to correct the level of tension V2 present at the exit of operational unit OP2.

The aforementioned $V_{max}$ and $V_{min}$ variable tension limits present on the aforementioned terminal V2 are intercepted by the two operational units OP3 and OP4 which are linked as comparators with hysteresis. The levels of tension where these two limits, $V_{max}$ and $V_{min}$, are chosen during the phase of setting by adjusting the trimmers "Ti" and "T2" respectively, for the superior (upper) and inferior (lower) limits. Such limits of tension are applied to the inverting entrances (inputs) of the operation (amplifier) units denominated by OP3 and OP4, while the non-inverting entrances of the aforementioned operational units are connected to terminal "V2 respectively, via the couple of resistors "T3-R8" and "T3-R9". The trimmer T3, during the phase of setting, regulates the hysteresis of the superior (upper) limits and that of the inferior (lower) limits. It also applies the exit tension "V2" to the non-inverting entrances of the amplifiers OP3 and OP4.

Whenever the tension applied to the non-inverting entrance of the comparator, operational unit OP3, through or via trimmer T3 surpasses the tension applied to its inverting entrance, the output of OP3 will rise. At its exit will be present the level of tension of the power supply and therefore it will bring the same level of tension to the control portal of the digital switch denominated by "DSW1". Such a switch, by closing, will charge the condenser C2 via the resistor R7.

As the value of tension present at the tips of such condenser C2 is applied to the non-inverting entrance of the operational unit OP1, the output also rises. This process of charging continues until the level of tension on the condenser C2 determines an increase in tension V1 at the exit of the operational unit OP1 and consequently through the switch SW and one of the resistances R2, R3, R4.

The aforesaid increase in tension from OP1 will be applied to the inverting entrance of the operational unit OP2. This will trigger a negative reaction (i.e., a counter reaction) at the exit of such operational unit OP2 with a related decrease of tension at the exit V2, such that it surpasses the level of hysteresis of the comparator OP3, which will allow the opening of the digital switch DSW1, in this way blocking the process of charging of the condenser C2.

In the same way, whenever the tension applied to the non-inverting entrance of the comparator OP4 through the trimmer T3 decreases below the level of tension applied to its inverting entrance, the tension present at it exit arrives at a level of mass (ground level "0") and therefore it brings the same level of tension to the control portal of the digital switch DSW3, causing DSW3 to open. This switch, when it opens, supplies through the resistor R10 the tension of the power supply to the control portal of the digital switch called DSW2 which upon closing, releases (i.e., discharges) the condenser C2 through the resistor R7. This process of release continues until the level of tension in the condenser C2 determines a decreases of tension V1 at the exit of the operational unit OP1 and consequently through the switch SW and one of the resistances R2, R3, R4.

Such decrease of tension of C2 will be applied to the inverting entrance of the operational unit OP2. This will trigger a negative reaction at the exit of such operational unit OP2 with a related increase of tension at exit V2, such as to surpass the level of hysteresis of the comparator OP4 which will allow the digital switch DSW2 to close through the digital switch DSW3, thus blocking the process of release of the condenser C2.

The variation in tension present at the tips of the exit terminal V2, taken from terminal 5 may have various possibilities of linking. For instance, a tension controlled audio frequency generator, or a MIDI interface audio generator, or a computerized interface portal, or a non-computerized one, or the management of systems of light mixing or electrical devices such as valves, pumps or electric engines or other servocontrols.

Such devices can have multiple uses, such as, for example, light and sound shows, play and entertainment, reproduction of artistic sound compositions through audiovisual supports, direct control of greenhouses, light sources, home and industrial uses, or it can allow the study of all phenomena linked to he sensitivity of the living biological organisms connected to the device.

Figure 3:
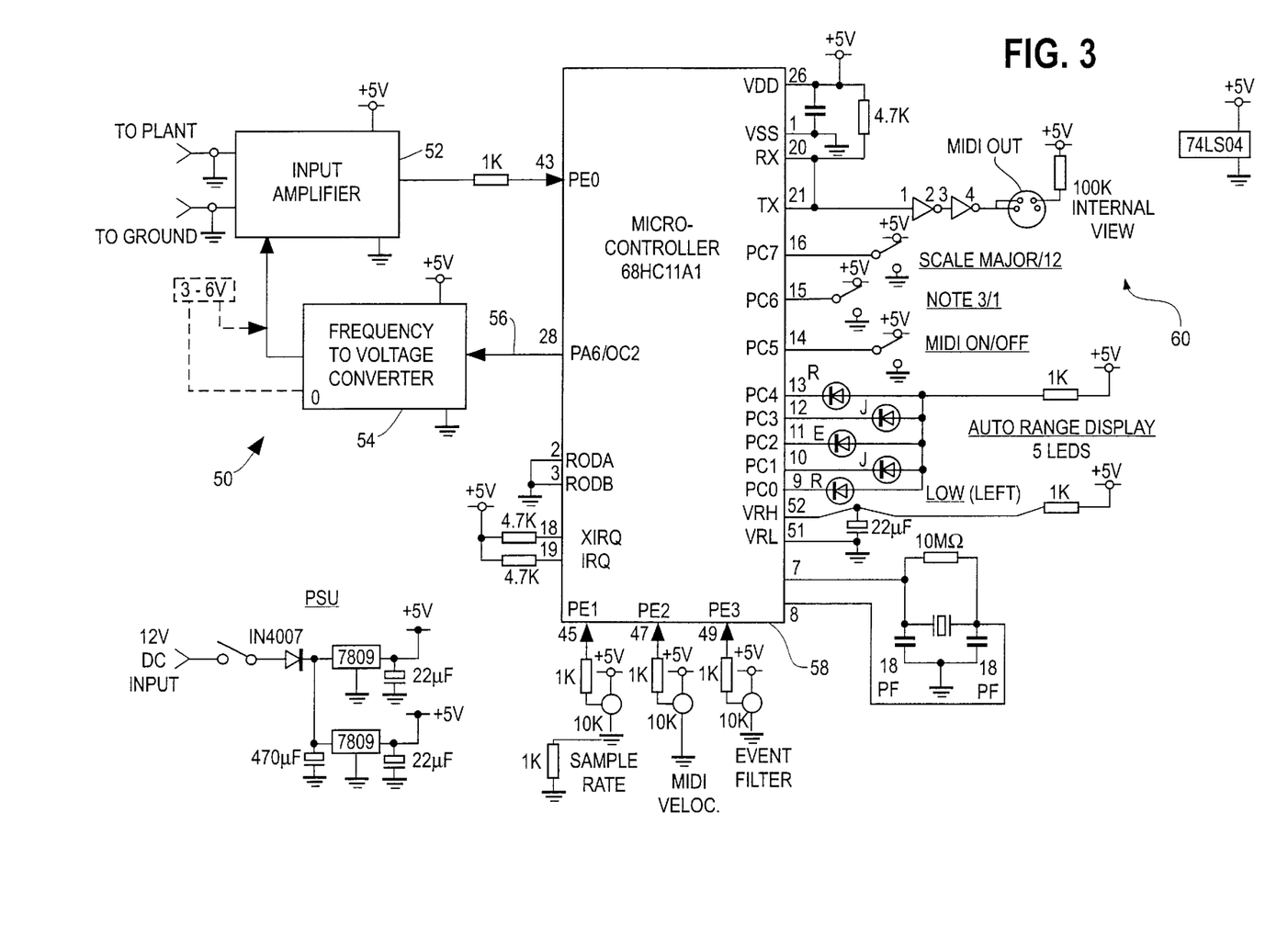
FIG. 3 depicts an interface circuit for the system of FIG. 1.
Figure 4:
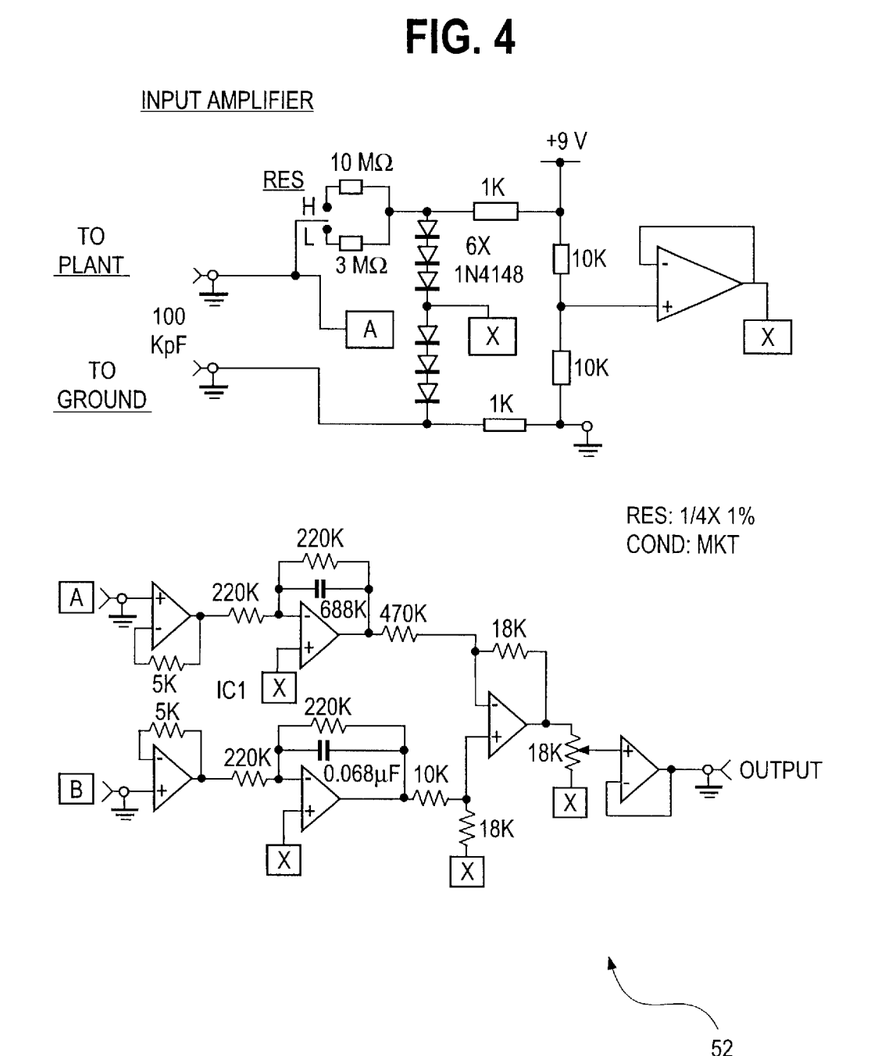
FIG. 4 depicts an amplifier for the circuit of FIG. 3.

FIG. 3 provides an example of an interface 50 that may be used to couple an output 5 of the microvariation detector 2 to other devices. As shown, the interface 50 may include an input amplifier (FIG. 4) 52 and a frequency to voltage converter (FIG. 5) 54.

Figure 5:
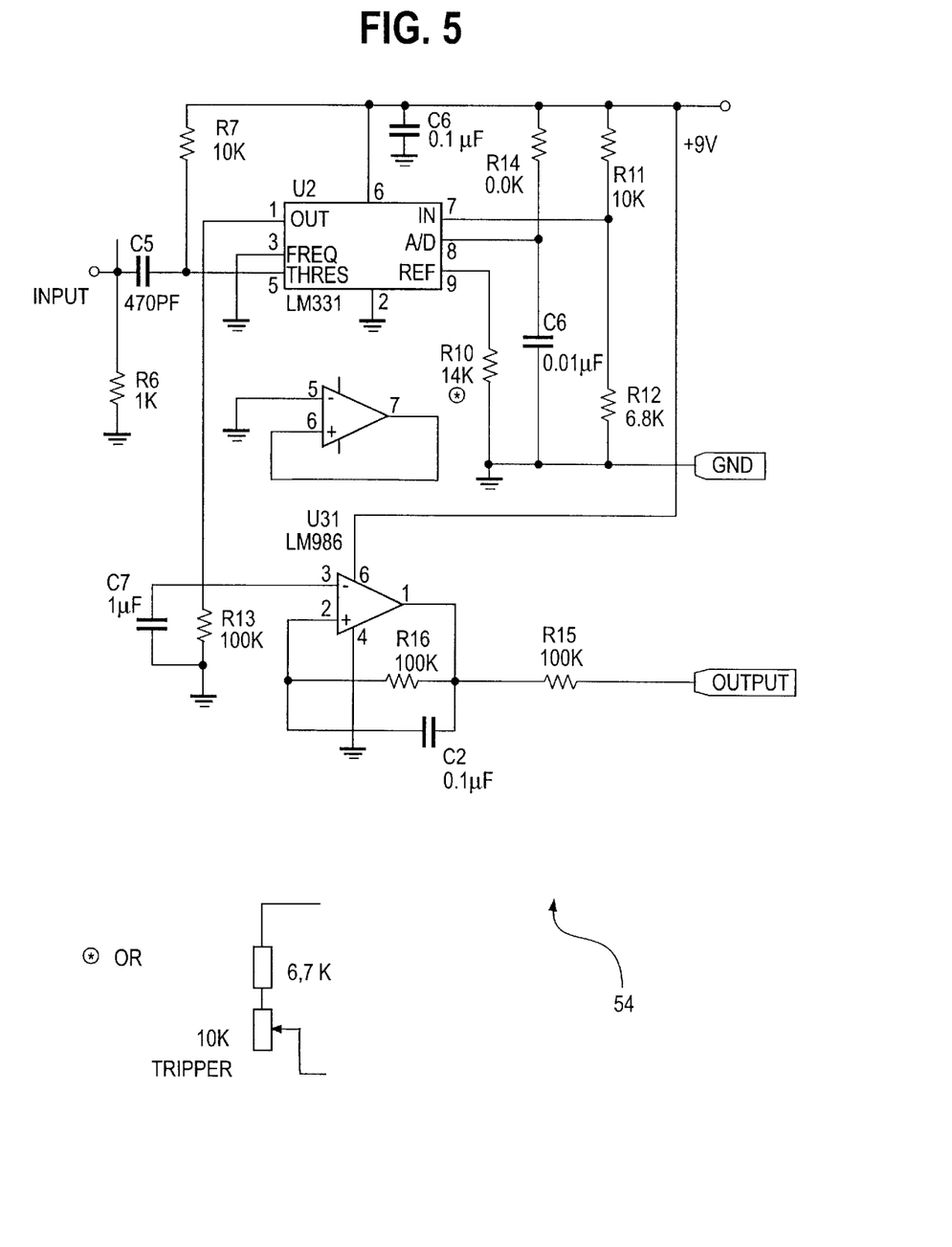
FIG. 5 depicts a frequency to voltage converter used by the circuit of FIG. 3.

The frequency to voltage converter 54 may be used to generate a direct current (DC) signal 56 that may be put to any of a number of uses. For example, the output 56 may be scaled to a 0–10 volt signal and used to control a variable speed fan (not shown) of a greenhouse. The DC signal 56 may also be used as a controlling signal of a power controller supplying UV grow lights in the greenhouse.

As mentioned above, the DC output 56 may also be used for light and sound shows. For example, the output 56 may be used as a controlling input signal through the use of microcontroller 58 (FIG. 3) or by direct connection to a music synthesizer (e.g., a Yamaha FM sound generator, OPL-x family of devices, sound card on a computer, etc.).

Where connected to a microcontroller 58, the DC output 56 may be detected on an input 28 of the microcontroller 58. The plant (operating through the microvariation detector 2) functions as an element (as a variable resistor) of the input Wheatstone bridge shown in FIG. 4. As the electrical resistance of the plant changes, an output of the Wheatstone bridge changes to provide a change in the output of the microvariation detector 2 in the range of from 40 mV to 4.80 mV. This voltage is converted into a digital form at the input 28 of the microcontroller 58 using an 8-bit analog to digital (A/D) converter. The 8-bit output of the A/D converter may then be used to retrieve a correct note code to emulate a MIDI keyboard. The note code is provided at a MIDI output 60. The steps used to retrieve the correct code using the microcontroller 58 is achieved using the object code of APPENDIX I.

Alternatively, the output of the microcontroller 58 may be provided as an input to a serial interface of a computer, which allows for the testing, analyzing and recording of the variations in external stimuli detected within the living organism. This provides for the tailoring of the specific sounds, the designation to selective mediums and eliminates external controls, filters and switches.

This may be accomplished by connecting the serial TX output of the microcontroller 58 to a MAX232 device through a 9-pin, d-edge connector and cable to the serial port of a computer. A standard DOS or windows communication program may be used to show data flow from the living organism 1. The only change to the microcontroller software is to provide a different baud rate (i.e., set the baud rate to 9,600, instead of the 31,200 baud used for the MIDI interface). The memory location "$B620" may also be loaded with a value "$30", instead of "$20".

Under an alternate embodiment of the invention (FIGS. 6, 7 and 8), variations in the resistance of the plant 1 are converted into a MIDI format which may be coupled through an output 100 to a music synthesizer (not shown).

Figure 6:
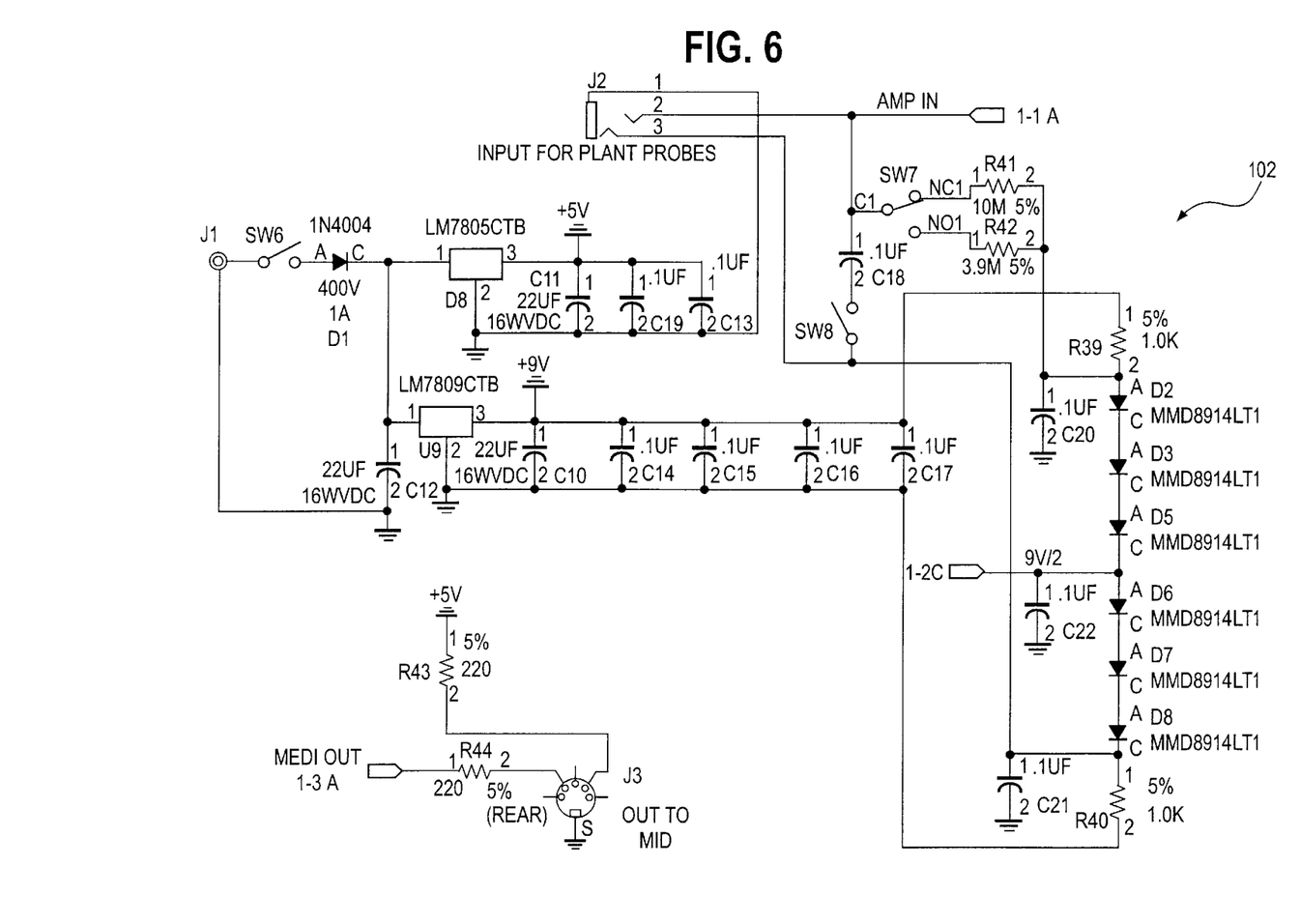
FIGS. 6 and 7, 7a–c depict a schematic of a circuit that may be used by the system of FIG. 1.
Figures 7, 7A:
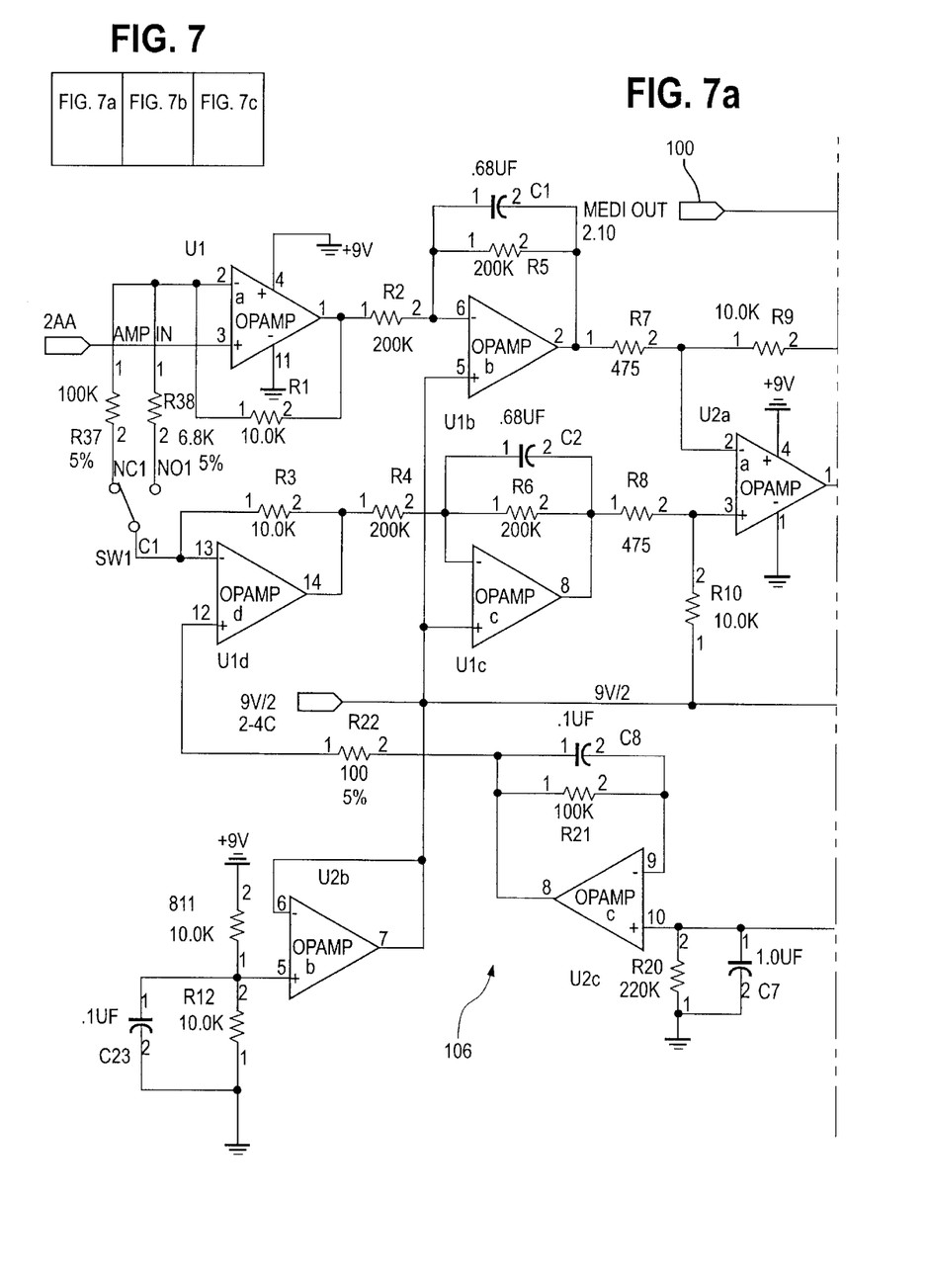
Figure 7B:
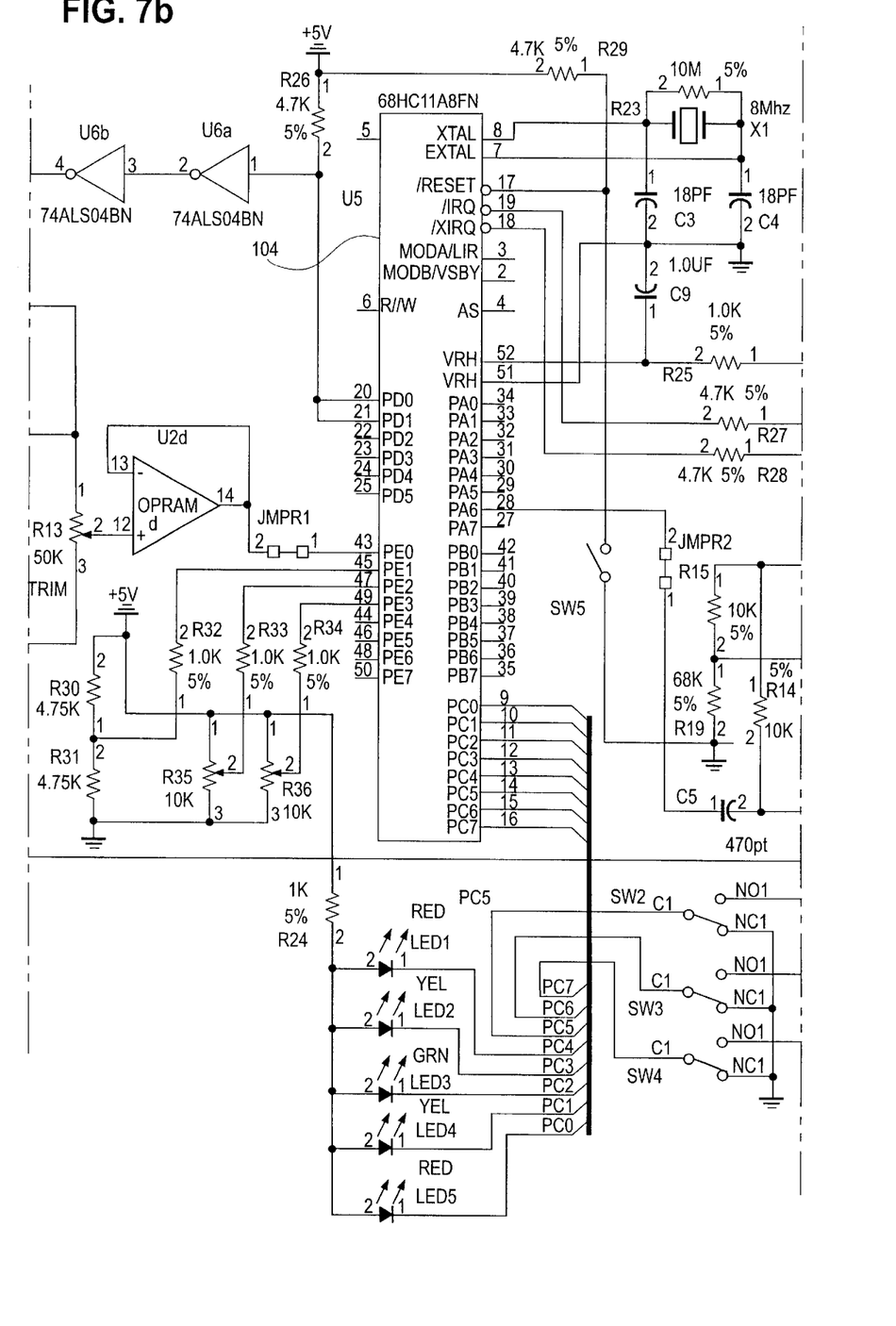
Figure 7C:
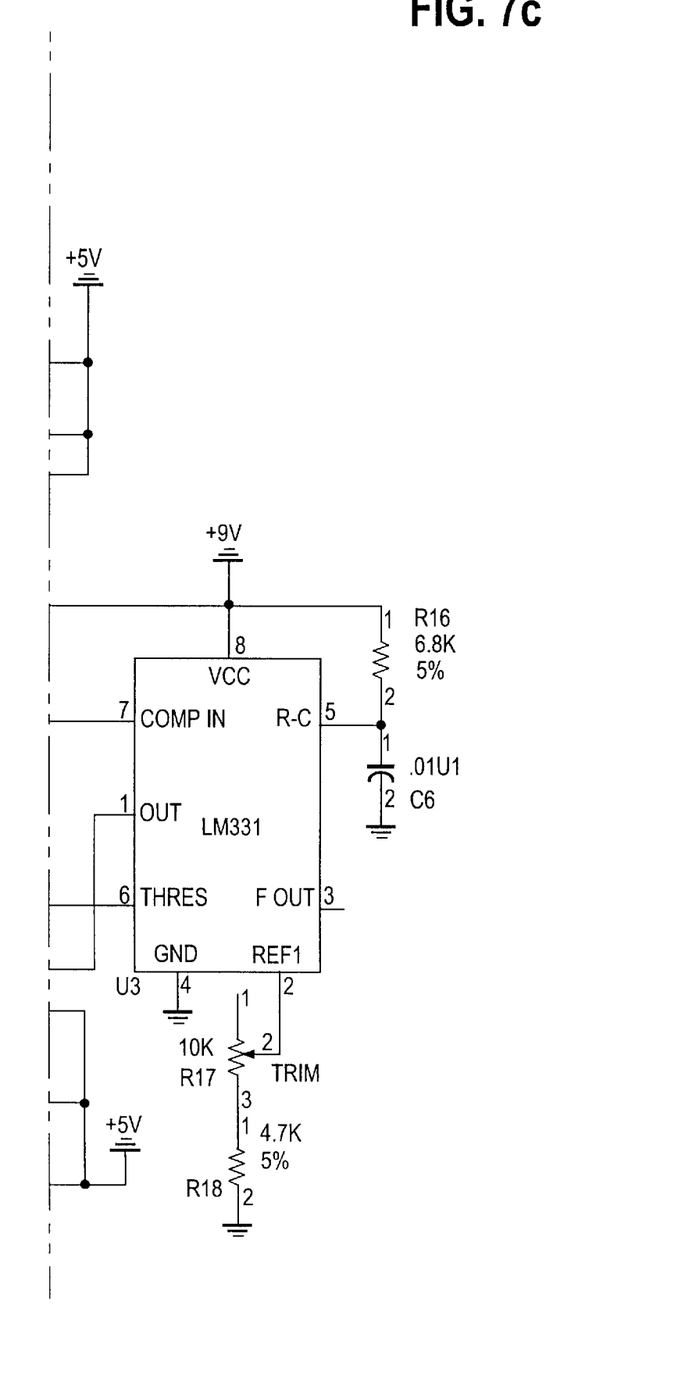
Figure 8:
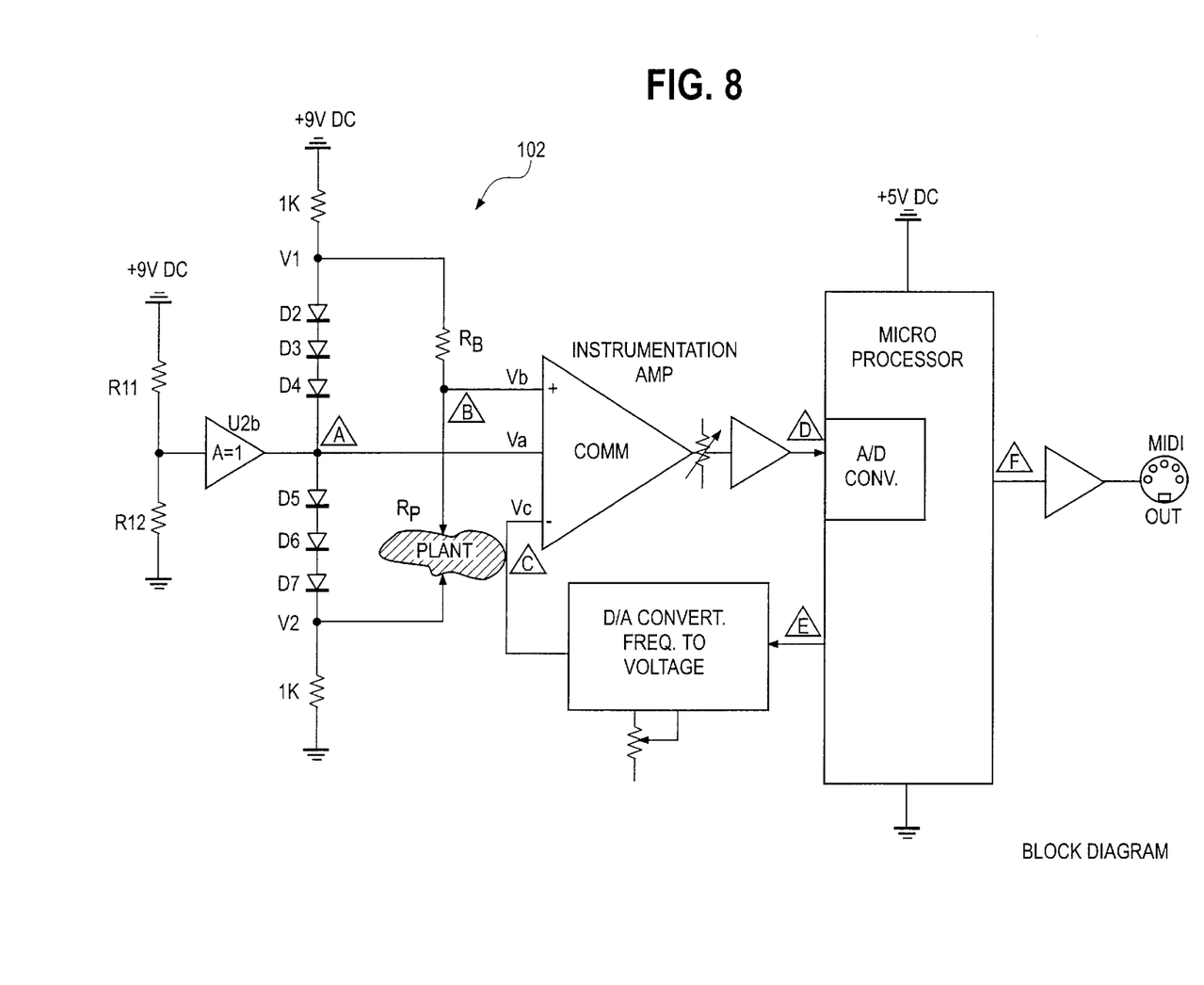
FIG. 8 is a simplified schematic of FIGS. 6 and 7.

FIGS. 6 and 7 are detailed schematics of the illustrated alternate embodiment. FIG. 8 is a simplified schematic that may be referred to as appropriate to an understanding of the illustrated alternate embodiment.

The plant 1 represents an element (a variable resistance) of a Wheatstone bridge (102, FIGS. 6 and 8), the other element being a selectable resistance Rb. The voltages V1 and V2 (FIG. 8) of the Wheatstone bridge 102 are established by the forward biased diode string made up of diodes D2 through D7. These diodes form a 4 volt, center tapped power source for the bridge 102. The reference resistor Rb is selectable as either a 10.1 Mega Ohm or as 4 Mega Ohm resistor (R41 or R42 in FIG. 6).

The other leg Rp of the bridge 102 is the resistance of the plant and soil combination. Variations in this resistance are detected by the microprocessor (FIGS. 7 and 8) and cause the microprocessor to output a serial MIDI command to a music synthesizer (e.g., a keyboard, sequence, PC sound card, etc.).

An output (i.e., the plant microvoltage) of the Wheatstone bridge 102 may be provided as an input to an instrumentation amplifier (FIG. 8). The instrumentation amplifier may be comprised of five operational amplifiers, U1a, U1b, U1c, U1d and U2a. A buffer amplifier U2d may be used-between the instrumentation amplifier and the microprocessor. The function of the instrumentation amplifier is to amplify the plant microvoltage caused by changes in the plant resistance Rp. The main gain stage U2a may have a fixed gain of 21. The gain of the input stages U1a and U1d may be selectable between 1.2 and 4. This results in a total gain of 25 in the difference voltage (Vb–Vc) referenced to a common connection Va.

The plant microvoltage of the bridge 102 is provided as one input, Vb, of the instrumentation amplifier. The other input, Vc, of the instrumentation amplifier is a feedback signal provided by a frequency to voltage converter (U3 and U2c). The feedback source of this frequency to voltage converter is an output of the microprocessor and the resulting voltage is subtracted from the plant microvoltage. The difference signal is amplified by the instrumentation amplifier and the output sent to an analog to digital converter (ADC) of the microprocessor.

In general, the circuit of FIGS. 6 and 7 forms a closed loop or feedback system in which the microprocessor and its associated program follows the changes in the resistance of the plant element and then create a counter signal to null out the change. This allows the device to follow very small changes in the plant element. As a result of this process, the microprocessor outputs a MIDI output (i.e., a serial output at 31,200 baud) which is representative of the change. An attached MIDI device (e.g., a keyboard) translates these signals into musical tones.

In order to generate musical tones, the microprocessor converts the analog output of the instrumentation amplifier into a digital value. The microprocessor then monitors the converted digital value to determine when that digital value has changed. For example, when the monitored digital value increases, the microprocessor may send a serial MIDI command string to activate a musical note via the UART of the microprocessor. Similarly, if the monitored value decreases, the microprocessor may turn off the note. If the monitored digital value is close to an upper or lower limit of the ADC range, then the microprocessor may change the frequency of the output to the frequency to voltage converter to bring the output of the instrument amplifier closer to a center of an operating range of the microprocessor's ADC converter range.

Turning now to the system, in detail, the Wheatstone bridge 102 (FIG. 6) balances the known resistance Rb (i.e., R41 or R42) against the varying resistance Rp of the plant 1 detected through pins 2 and 3 of plug J2. One side of the bridge 102 may include the series-connected set of diodes D2, D3, D5, D6, D7, D8 (discussed above) and resistors R39 and R40. A center point of the diodes provides a reference voltage Va through pin 1–2C to differential amplifiers U1b and U1c.

The other side of the Wheatstone bridge is formed by the plant 1 and known resistance Rb (i.e., R41 or R42). A center point passing from pin 1–1A on FIG. 6 to pin 2–4A on FIG. 7 carries the plant microvoltage to amp U1a. A selector switch SW1 provides the adjustable gain within the op-amp U1a of either 1.2 or 4.0.

A second amp U1d receives the feedback signal from the processor 104. The feedback signal and plant microvoltage are each normalized against the voltage reference from the Wheatstone bridge 103 in amps U1b and U1c and applied to the differential inputs of amp U2a. Amp U2a generates the difference signal (i.e., Vb−Vc) between the plant microvoltage and feedback signal. The difference signal is amplified in amp U2d and provided as an input to the processor 104.

Within the MIDI converter processor 104, the difference signal is converted into a MIDI format. An output 100 under the MIDI protocol may be provided to the music synthesizer thereby producing the music described above.

In order to increase the stability of the system, the processor 104 provides a variable frequency signal on pin 28. A threshold detector LM331 (U3) detects and amplifies the pulses. An integrator 106 (i.e., with a time constant of approximately 220 ms) integrates the pulse train to produce the feedback signal of the frequency to voltage converter.

The frequency to voltage converter accepts the varying frequency output of the microprocessor and converts it to a voltage that is proportional to that frequency. The resulting voltage is applied to the negative input of the instrument amplifier, as discussed above. Also as discussed above, this voltage is subtracted by the instrument amplifier from the plant microvoltage on the positive input. The feedback from the frequency to voltage converter allows the device 10 to follow large, slow changes from the bridge 102 and also provide the ability to detect small changes which determine which determine which notes are played through the attached MIDI synthesizer device.

A number of switches may be provided to enhance music quality. A first switch SW3 may be used to select intervals between musical notes. A second switch SW4 may be used to select a scale (e.g., a major scale or a 12 round scale).

The foregoing detailed description has been given for clearness of understanding only, and no unnecessary limitation should be understood therefrom, as modifications will be obvious to those skilled in the art.

What is claimed is:

1. A method of using micro-variations of a biological living plant organism to generate music, such method comprising the steps of:
   detecting a plant microvoltage across a varying resistance of the biological living plant organism within a Wheatstone bridge;
   generating a feedback signal from an output of an external MIDI sound generator;
   subtracting the feedback signal from the plant microvoltage to provide a difference signal; and
   providing the difference signal as a drive signal to the MIDI sound generator to generate musical tones.

2. The method of using micro-variations of the biological living plant organism to generate music as in claim 1 wherein the step of detecting a plant microvoltage across a varying resistance of the biological living plant organism within a Wheatstone bridge further comprises balancing the varying resistance against a known resistance.

3. The method of using micro-variations of the biological living plant organism-to generate music as in claim 2, wherein the step of generating the feedback signal further comprises integrating a variable frequency pulse train from the output of the MIDI sound generator.

4. The method of using micro-variations of the biological living plant organism to generate music as in claim 2 further comprising connecting the biological living plant organism and known resistance in series.

5. The method of using micro-variations of the biological living plant organism to generate music as in claim 4 further comprising connecting an even number of series-connected diodes in parallel with the series connected plant and known resistance.

6. The method of using micro-variations of the plant to generate music as in claim 5 further comprising connecting a reference voltage to a center point of the series-connected diodes.

7. The method of using micro-variations of the plant to generate music as in claim 6 further comprising detecting the plant microvoltage from a center point of the series-connected plant and known resistance.

8. An apparatus for using micro-variations of a biological living plant organism to generate music, such apparatus comprising:
   means for detecting a plant microvoltage across a varying resistance of the biological living plant organism within a Wheatstone bridge;
   means for generating a feedback signal from an output of an external MIDI sound generator;
   means for subtracting the feedback signal from the plant microvoltage to provide a difference signal; and
   means for providing the difference signal as a drive signal to the MIDI sound generator to generate music.

9. The apparatus for using micro-variations of the biological living plant organism to generate music as in claim 8 wherein the means for detecting a plant microvoltage across a varying resistance of the biological living plant organism within a Wheatstone bridge further comprises means for balancing the varying resistance against a known resistance.

10. The apparatus for using micro-variations of the biological. living plant organism to generate music as in claim 9, wherein the means for generating the feedback signal further comprises means for integrating a variable frequency pulse train from the output of the MIDI sound generator.

11. The apparatus for using micro-variations of the biological living plant organism to generate music as in claim 8 further comprising means for connecting the biological living plant organism and known resistance in series.

12. The apparatus for using micro-variations of the biological living plant organism to generate music as in claim 11 further comprising means for connecting an even number of series-connected diodes in parallel with the series connected plant and known resistance.

13. The apparatus for using micro-variations of the plant to generate music as in claim 12 further comprising means for connecting a reference voltage to a center point of the series-connected diodes.

14. The apparatus for using micro-variations of the plant to generate music as in claim 13 further comprising means for detecting the plant microvoltage from a center point of the series-connected plant and known resistance.

15. An apparatus for using micro-variations of a biological living plant organism to generate music, such apparatus comprising:
 a Wheatstone-bridge providing a plant microvoltage across a varying resistance of the biological living plant organism;
 a feedback loop providing a feedback signal from an output of an external MIDI sound generator;
 a differential amplifier subtracting the feedback signal from the plant microvoltage to provide a difference signal; and
 a drive amplifier providing the difference signal as a drive signal to the MIDI sound generator to generate music.

16. The apparatus for using micro-variations of the biological living plant organism to generate music as in claim 15 wherein the Wheatstone bridge further comprises a known resistance adapted for balancing against the varying resistance.

17. The apparatus for using micro-variations of the biological living plant organism to generate music as in claim 16, wherein the feedback loop further comprises an integrator adapted to integrate a variable frequency pulse train from the output of the MIDI sound generator.

18. The apparatus for using micro-variations of the biological living plant organism to generate music as in claim 15 further comprising the biological living plant organism and known resistance connected in series.

19. The apparatus for using micro-variations of the biological living plant organism to generate music as in claim 18 further comprising an even number of series-connected diodes connected in parallel with the series connected plant and known resistance.

20. The apparatus for using micro-variations of the plant to generate music as in claim 19 wherein the series connected diodes further comprises a center point for providing a reference voltage.

21. A method of using micro-variations of a biological living plant organism to generate music, such method comprising the steps of:
 detecting a plant microvoltage across a varying resistance of the biological living plant organism within a Wheatstone bridge;
 providing the plant microvoltage as a driving signal to an external MIDI sound generator; and
 generating a feedback signal from an output of the MIDI sound generator; and
 substantially reducing the driving signal with the feedback signal.

* * * * *